United States Patent [19]

Elkins et al.

[11] Patent Number: 4,898,702
[45] Date of Patent: Feb. 6, 1990

[54] METHOD AND APPARATUS FOR REMOVAL OF A WIRE MANDREL FROM A CATHETER

[75] Inventors: Jeffrey M. Elkins, Miami Lakes; Russell F. Collins, Hialeah, both of Fla.

[73] Assignee: Cordis Corporation, Miami, Fla.

[21] Appl. No.: 177,062

[22] Filed: Apr. 4, 1988

[51] Int. Cl.⁴ ............................................. B29C 41/42
[52] U.S. Cl. ................................. 264/145; 264/149; 264/159; 264/166; 264/334; 425/308; 425/438
[58] Field of Search ............... 264/166, 165, 138, 149, 264/159, 150, 163, 317, 334, 145, 172; 425/215, 225, 436 R, 436 RM, 438, 308

[56] References Cited

U.S. PATENT DOCUMENTS

| | | | |
|---|---|---|---|
| 2,013,684 | 9/1935 | Capella-Dalmau | 264/335 |
| 2,330,370 | 9/1943 | Miller | 264/145 |
| 2,418,974 | 4/1947 | Henry | 425/393 |
| 2,561,569 | 7/1951 | Flynn | 264/149 |
| 2,959,847 | 11/1960 | Hohl | 425/438 |
| 3,284,852 | 11/1966 | Boggs | 425/436 R |
| 3,585,707 | 6/1971 | Stevens | 29/427 |
| 3,668,288 | 6/1972 | Takahashi | 264/47 |
| 3,690,796 | 9/1972 | Borsvold | 264/166 |
| 3,946,483 | 3/1976 | Holden et al. | 29/427 |
| 4,201,535 | 5/1980 | Ninneman | 425/548 |
| 4,218,419 | 8/1980 | Alfio | 264/334 |
| 4,246,225 | 1/1981 | Ninneman | 264/336 |
| 4,284,459 | 8/1981 | Patel et al. | 156/245 |
| 4,291,453 | 9/1981 | Mathieu | 264/149 |
| 4,311,654 | 1/1982 | Blandin | 264/213 |
| 4,321,226 | 3/1982 | Markling | 264/150 |
| 4,484,586 | 11/1984 | McMickle et al. | 264/165 |
| 4,490,316 | 12/1984 | Satzler | 264/40.7 |
| 4,551,292 | 11/1985 | Fletcher et al. | 264/139 |
| 4,629,650 | 12/1986 | Kataoka | 264/45.9 |
| 4,764,324 | 8/1988 | Burnham | 264/150 |

FOREIGN PATENT DOCUMENTS 2357275 6/1974 Fed. Rep. of Germany .
62-85923 4/1987 Japan .

Primary Examiner—Jeffery Thurlow
Attorney, Agent, or Firm—Watts, Hoffmann, Fisher & Heinke

[57] ABSTRACT

A catheter fabrication method and apparatus. Two rotating contact rollers define a nip to engage a mandrel used in fabricating an elongated tubular catheter. The rollers pull the mandrel from the catheter as a retaining block prevents the catheter from moving with the mandrel. The rollers rotate in opposite directions and are driven by a variable speed direct current motor.

7 Claims, 2 Drawing Sheets

METHOD AND APPARATUS FOR REMOVAL OF A WIRE MANDREL FROM A CATHETER

TECHNICAL FIELD

The present invention relates to the field of manufacturing extruded catheters and more particularly relates to removal of wire mandrels from tubular extruded catheters.

BACKGROUND OF THE INVENTION

A commonly used technique for fabricating a catheter is to extrude a synthetic tubular sheath about an elongated, cylindrical mandrel and then to remove the mandrel from the sheath. Different size catheters for different invasive procedures are formed by using different diameter and different length mandrels. One example of a prior art catheter fabrication method is disclosed in U.S. Pat. No. 3,585,707 to Stevens. The disclosure of the '707 patent is incorporated herein by reference.

In accordance with the teaching of the Stevens patent, a flexible tubular catheter is constructed by extruding a plastic sheath onto a ductile wire mandrel. A braided layer of fine wire is tightly wound over the plastic coating and then a second plastic layer is extruded over the braided sheath. After a catheter sheath has been constructed in this fashion, the center wire mandrel is stretched to elongate the wire, thereby reducing its diameter and facilitating removal from the catheter sheath.

One technique that has developed in conjunction with the practice of the invention disclosed in the aforementioned '707 Patent is the use of a silver or nickel-silver coating on a copper wire mandrel. This coating facilitates removal of the catheter after it is extruded onto the mandrel. Experience with silver coated mandrels suggests that some of the coating may blister off the copper wire during the separation process. In addition, coating the wire mandrel increases the cost of fabricating the catheter.

Another disadvantage of the method described in Stevens is that a piece of the catheter must be removed from each end of the mandrel prior to mandrel separation, reducing the yield.

DISCLOSURE OF THE INVENTION

These disadvantages of the prior art are overcome by a method for fabricating a catheter during which one extrudes a plastic tubular layer over a wire mandrel to a desired thickness, exposes a portion of the mandrel at one end, pushes the exposed portion of the mandrel through a passageway in a body which has a diameter wide enough to receive the mandrel but not the extrusion and gripping and pulling the mandrel through the body while the body restrains the movement of the extrusion.

One advantage of the present invention is that the mandrel may be removed without the need for an expensive silver coating. Furthermore, since the mandrel is not coated or stretched the risk that metallic particles broken off the mandrel will contaminate the catheter lumen is greatly reduced. Yet another advantage of the present invention is that only one end of the mandrel need be exposed, so that the yield is increased.

Another aspect of the invention is to accomplish the gripping and pulling of the mandrel by pushing the exposed end of the mandrel into a nip between two contact wheels and turning the wheels in a counter-rotating direction so as to draw the mandrel through the body.

Yet another aspect of the invention is an apparatus for removing a wire mandrel from a plastic tubular extrusion to form an elongated catheter including a body having a through passage with a diameter greater than that of the wire mandrel but less than that of the plastic extrusion. A drawer grips an exposed portion of the mandrel and pulls the mandrel through the body while the body restrains the motion of the extrusion.

Still another aspect of the invention is that the drawer includes a pair of rotatably mounted rollers spaced to form a nip for grasping the exposed end of the mandrel and separating the mandrel from the tubular extrusion.

Yet another aspect of the invention is the use of a motor to turn the rollers.

Still another aspect of the invention is that the surface of the drawer which contacts the exposed portion of the mandrel be roughened to improve the drawer's grip on the mandrel.

From the above, it is appreciated that one object of the invention is a new and improved method and apparatus for removing a mandrel from an extruded catheter. This and other objects, features and advantages of the invention will become better understood from a detailed description of the invention when considered in conjunction with the accompanying drawings.

BEST MODE FOR PRACTICING THE INVENTION

Figure 1:
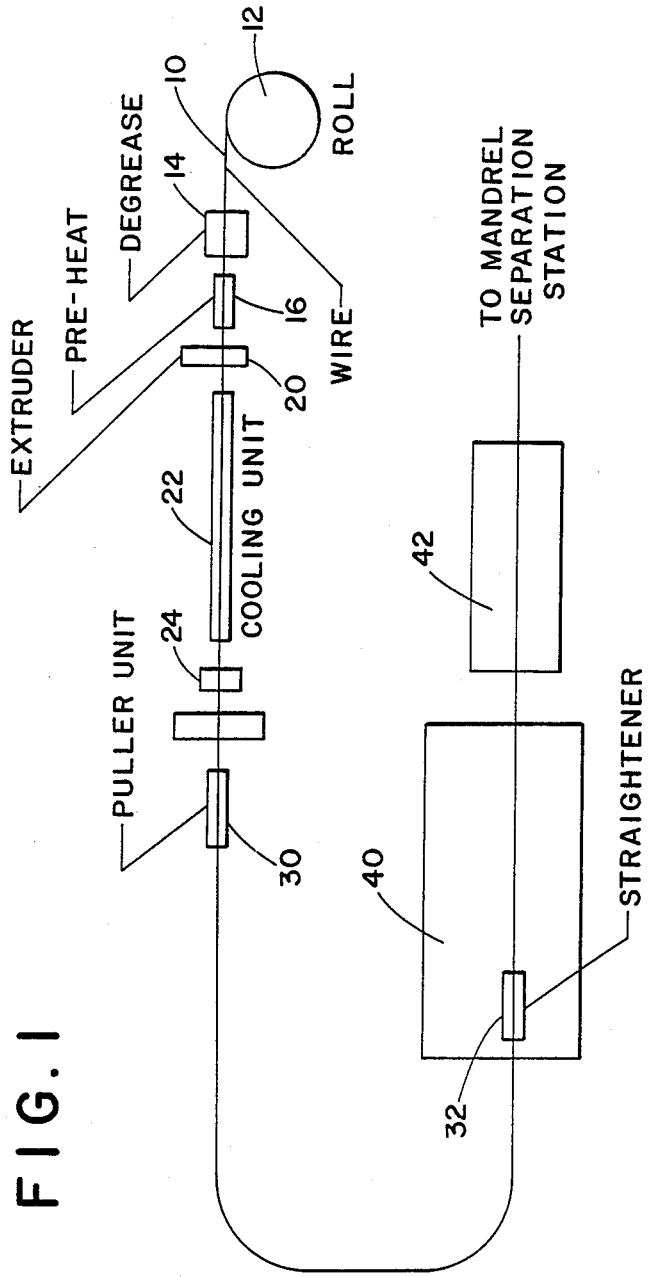
FIG. 1 is a schematic drawing showing different phases of a catheter fabrication procedure.

Turning now to the drawings, FIG. 1 is a schematic depiction of a number of phases practiced in fabricating a tubular extruded catheter. The catheter most typically is a braided catheter so that the extrusion process takes place in two steps: a first extruded layer is formed on a mandrel, a wire braid is wound over the first extruded layer and a second extruded layer is applied to cover the braid. One material suitable for extrusion in the fabrication of a catheter is polyurethane.

A wire mandrel 10 is shown stored on a supply 12 and unwound from the supply by a puller unit 30. The wire first passes through a degreaser 14. Once the wire mandrel 10 has been degreased, it is pre-heated by a heater 16 and one or more extruded layers of plastic are applied to the wire 10 by an extruder 20. The combination of the wire mandrel 10 and one or more extruded layers passes through a cooling unit 22 which typically cools the combination by directing a jet of water into direct contact with the elongated plastic extrusion. Cooling the extrusion and mandrel before separation necessitates a greater removal force but increases yield.

Downstream from the cooling unit 22 a jet of air is applied to the elongated extrusion by an air dryer 24. The combined extrusion and mandrel is then engaged by the puller unit 30 which pulls the extruded plastic through the previous steps.

Downstream from the puller unit 30, a wire straightener 32 engages the combined mandrel and extruded catheter to exert a straightening process in preparation for cutting and stripping away a short length of the catheter material at one end of the cut piece. Both the straightening and cutting are accomplished at a combined cut and strip station 40. The wire straightener serves to loosen the extrusion from the mandrel. The loosened extrusion, in turn, contracts on the mandrel, perhaps exposing enough of one end of the mandrel to avoid the need for trimming the catheter before removal of the mandrel.

Subsequent to the cut and strip station station 40, individual catheter segments have been cut to an appropriate catheter size length and a small length of the mandrel at one end of each segment has been exposed. These catheter link segments are then either stacked by an automated stacker 42 in preparation for transfer to a mandrel separation station or loaded directly into an automated mandrel separation hopper.

Figure 3:
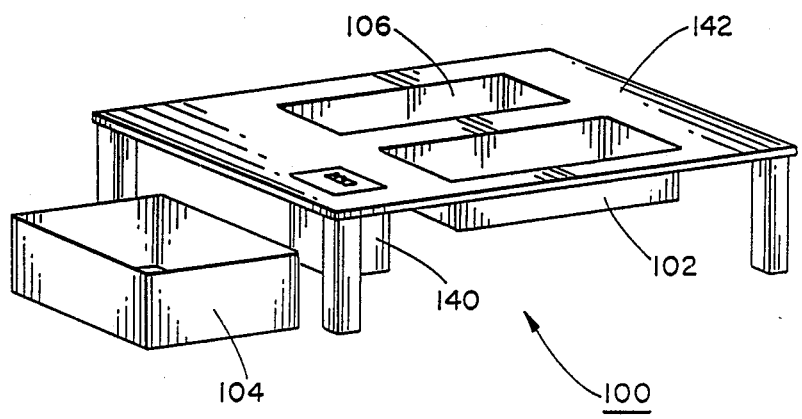
FIG. 3 shows one version of a mandrel separation station utilizing the FIG. 2 apparatus.

The mandrel separation station 100 is depicted in FIG. 3. In accordance with the present use of the invention, mandrel separation is accomplished by an operator withdrawing catheter-length segments of the catheter and attached mandrel from a first storage bin 102, separating the mandrel from the catheter in such a way that individual mandrel pieces are ejected from the workstation 100 into a mandrel storage bin 104 and placing the catheters having center passageways defined by the region previously occupied by the mandrel into a third storage bin 106.

Figure 2:
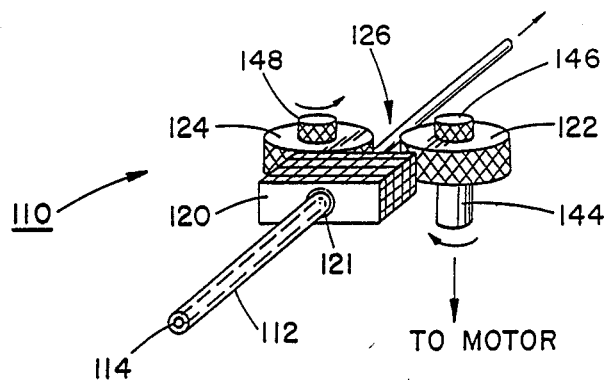
FIG. 2 is a perspective view of a mandrel separation apparatus.

FIG. 2 schematically depicts an apparatus 110 for separating a plastic catheter 112 from a wire mandrel (preferrably silver-coated copper) 114. A short (approximately 0.5 to 0.75 inch) segment of the mandrel 114 is exposed at one end of the catheter 112 at the cut and strip station 40 (FIG. 1). This exposed end of the mandrel 114 is inserted into a retaining block 120 which defines a throughpassage wide enough to accommodate the mandrel 114 but narrower than the catheter 112. As the operator pushes the mandrel through the retaining block 120, an exposed end of the mandrel 114 passes through the retaining block 120 and is engaged by two contact rolls 122, 124 rotating in opposite directions which define a nip 126 for grasping the exposed mandrel 114 and exerting a separating force to withdraw the mandrel from within the catheter 112. The two contact rolls 122, 124 are spring biased toward each other so that without a mandrel between them they do not touch but are separated by a distance less than the mandrel diameter. They are symmetric about a center of the passage 121 so that as the the mandrel 114 is pushed through the block 120 it contacts both rolls 122, 124 at approximately the same time. Since the retaining block through passage is only large enough to accommodate the mandrel, one end of the catheter 112 abuts the retaining block and is held stationary as the rotating rolls 122, 124 pull the mandrel 114 through the catheter.

The contact rolls 122, 124 are each connected to a motor. The rates of rotation of these rolls are approximately the same but each turns oppositely the other. A preferred motor (not shown) is fixed within a motor support housing 140 coupled to a table 142 that supports both storage bins 102, 106. A preferred motor comprises a variable speed direct current powered motor having an output shaft 144 for driving the rolls 122, 124. A transmission from the motor assures that both rolls rotate at the same speed.

The outer surfaces of the two rolls 122, 124 are roughened to enhance frictional engagement with the mandrel 114. If, as is preferred, the contact rolls are made of tool steel, they should never need replacing when used with silver-coated mandrels. Were the roughened surfaces of the rolls to become smooth, however, the rolls may be replaced. The motor shaft 144 includes a threaded end portion so that a threaded nut 146 can be loosened and the roll 122 lifted off the end of the shaft 144 and replaced. A similar threaded shaft (not shown) supports the roll 124 to allow a nut 148 to be removed for replacement of the roll 124. Although a preferred motor comprises an direct current variable speed motor, an alternating current motor having a controllable output speed is suitable.

The invention has been described with a degree of particularity. It is the intent, however, that the invention include all modifications and alterations from the disclosed design falling within the spirit or scope of the appended claims.

We claim:

1. A method for fabricating a catheter comprising the steps of: extruding a plastic tubular layer over a wire mandrel to a desired thickness to form a catheter; exposing a portion of the mandrel at one end; pushing the exposed portion of the mandrel through a passageway in a body, said passageway having a diameter wide enough to receive the mandrel but not the extrusion;
   pushing the exposed end of the mandrel into a nip between two contact wheels; and
   turning the wheels, whereby the mandrel is withdrawn from the catheter.

2. The method of claim 1 wherein prior to the step of exposing a portion of the mandrel at one end the combined extrusion and mandrel is passed through a wire straightener to loosen the engagement between the extrusion and the mandrel.

3. An apparatus for removing a wire mandrel from a plastic tubular extrusion to form an elongated catheter, an exposed portion of said mandrel extending beyond one end of the plastic tubular extrusion, comprising:
   a body having a throughpassage with a diameter greater than that of the wire mandrel but less than that of the plastic extrusion; and
   gripping means for gripping the exposed portion of the mandrel and pulling the mandrel through the body while the body restrains the motion of the plastic tubular extrusion;
   said gripping means comprising a pair of rotatably mounted rollers spaced near the throughpassage in the body to form a nip for grasping the exposed end of the mandrel as the mandrel is pushed through the body and pulling the mandrel from the tubular extrusion.

4. The apparatus of claim 3, wherein a surface of one of the mounted rollers which contacts the wire mandrel is roughened to facilitate grasping the wire mandrel.

5. The apparatus of claim 3 including a wire straightener positioned along a travel path for the combined tubular extrusion and wire mandrel to receive the extrusion and mandrel and loosen an engagement between the extrusion and the mandrel before the tubular extrusion is separated from the mandrel by the gripping means.

6. The apparatus of claim 3 including means for rotating one of the rollers, whereby the rollers cooperate to pull the wire mandrel through the body.

7. The apparatus of claim 6 wherein the means for rotating the wheels includes a motor.

* * * * *